(12) United States Patent
Yang et al.

(10) Patent No.: US 11,731,892 B2
(45) Date of Patent: Aug. 22, 2023

(54) NOVOSPHINGOBIUM SP. SJB007 AND APPLICATION THEREOF IN REMOVAL OF PHOSPHORUS FROM WASTEWATER

(71) Applicant: Wenzhou University, Zhejiang (CN)

(72) Inventors: Hailong Yang, Zhejiang (CN); Huabin Zhou, Zhejiang (CN); jiebing Sun, Zhejiang (CN); liang Zhang, Zhejiang (CN); shimiao Zhou, Zhejiang (CN)

(73) Assignee: Wenzhou University, Zhejiang (CN)

( * ) Notice: Subject to any disclaimer, the term of this patent is extended or adjusted under 35 U.S.C. 154(b) by 102 days.

(21) Appl. No.: 17/408,503

(22) Filed: Aug. 23, 2021

(65) Prior Publication Data

US 2022/0380240 A1 Dec. 1, 2022

(51) Int. Cl.
| | |
|---|---|
| C02F 3/30 | (2023.01) |
| C12N 1/20 | (2006.01) |
| C02F 3/34 | (2023.01) |
| A01G 27/00 | (2006.01) |
| C12R 1/01 | (2006.01) |
| C02F 101/10 | (2006.01) |
| C02F 103/20 | (2006.01) |

(52) U.S. Cl.
CPC ............ C02F 3/308 (2013.01); A01G 27/003 (2013.01); C02F 3/34 (2013.01); C12N 1/205 (2021.05); A01G 27/00 (2013.01); C02F 2101/105 (2013.01); C02F 2103/20 (2013.01); C02F 2209/02 (2013.01); C02F 2209/06 (2013.01); C12R 2001/01 (2021.05); Y02W 10/10 (2015.05)

(58) Field of Classification Search
CPC ...... C02F 3/308; C02F 3/34; C02F 2101/105; C02F 2103/20; C02F 2209/02; C02F 2209/06; A01G 27/003; A01G 27/00; C12N 1/205; C12R 2001/01

USPC ................. 210/605, 601, 612, 906
See application file for complete search history.

(56) References Cited

U.S. PATENT DOCUMENTS

2019/0071335 A1* 3/2019 Zhou .................. C12P 3/00

FOREIGN PATENT DOCUMENTS

| CN | 105779344 A | * 7/2016 |
| KR | 20150001055 A | * 1/2015 |

OTHER PUBLICATIONS

Machine-generated English translation of CN 105779344, generated on Jan. 27, 2023.*
Machine-generated English translation of KR 20150001055, generated on Jan. 27, 2023.*

(Continued)

*Primary Examiner* — Fred Prince
(74) *Attorney, Agent, or Firm* — JCIP Global Inc.

(57) ABSTRACT

The invention relates to a *Novosphingobium* sp. SJB007 and an application thereof in removal of phosphorus from wastewater, belonging to the technical field of environmental microorganisms. One aspect of the invention provides a *Novosphingobium* sp. SJB007 with an access number of CGMCC (China General Microbiological Culture Collection Center) No. 21177. Another aspect of the invention provides an application of the *Novosphingobium* sp. SJB007 in removal of phosphorus from wastewater. The efficient phosphorus-accumulating strain *Novosphingobium* sp. SJB007 provided by the invention has a high removal rate of more than 97% when the concentration of phosphorus in the wastewater is 10-30 mg/L under an appropriate condition.

5 Claims, 1 Drawing Sheet
Specification includes a Sequence Listing.

(56) References Cited

OTHER PUBLICATIONS

Zhu Weiqiang et al., "Selection of two denitrifying phosphorus-accumulating bacterium and their influencing factors", Industrial Water Treatment, vol. 10, Issue 6, Jun. 2016, with English abstract, pp. 3295-3306.
Zhang Licheng et al., "Research On the Screening and characteristics of Nitrosation Denitrifying Dephosphorization of Five Strains of Phosphate Accumulating Organisms", Industrial Water Treatment, vol. 32, Issue 4, Jan. 2012, with English abstract, pp. 33-35.
B. Acevedo et al., "The metabolic versatility of PAOs as an opportunity to obtain a highly P-enriched stream for further P-recovery", Chemical Engineering Journal, vol. 270, Jun. 2015, pp. 459-467.
Wei Ru-Ping et al., "Research Progress on the Functional Microorganisms in Enhanced Biological Phosphorus Removal (EBPR) Systems", Biotechnology Bulletin, vol. 33, Issue 10, Jul. 2017, with English abstract, pp. 1-8.

\* cited by examiner

NOVOSPHINGOBIUM SP. SJB007 AND APPLICATION THEREOF IN REMOVAL OF PHOSPHORUS FROM WASTEWATER

BACKGROUND

Technical Field

The present invention belongs to the technical field of environmental microorganisms, in particular to a *Novosphingobium* sp. SJB007 and an application thereof in removal of phosphorus from wastewater.

Description of Related Art

Algae overgrowth caused by water eutrophication is one of the main causes that lead to deterioration of water quality. As an important factor leading to water eutrophication, phosphorus has a pollution source mainly from domestic, industrial and agricultural wastewater. Therefore, one of the main objects of wastewater treatment is to remove phosphorus from wastewater.

A traditional physicochemical phosphorus removal process suffers low efficiency, complicated technology and high possibility of secondary pollution. In contrast, the biological phosphorus removal process features low cost, small workload, high efficiency and wide application range, and thus is the main process for removal of phosphorus from wastewater at current. In the biological phosphorus removal process, microorganisms, i.e., phosphorus accumulating organisms play a leading role, which can contribute to anaerobic phosphorus release and aerobic or anoxic excessive phosphorus uptake under the alternative operation of anaerobic/aerobic or anaerobic/anoxic conditions. The phosphorus content in these microorganisms is multiple times more than that of common bacteria. The existing studies believe that the phosphorus accumulating organisms include aerobic phosphorus accumulating organisms and denitrifying phosphorus accumulating organisms. The biological phosphorus removal strains as reported mainly include strains of *Pseudomonas* (Zhu Weiqiang, Chen Shu and Zhang Peiyu, Selection of Two Denitrifying Phosphorous-accumulating Bacterium and Their Influencing Factors, Chinese Journal of Environmental Engineering, 2016, 10(4): 3295-3302), *Enterobacter, Staphylococcus, Paracoccus* and *Pantoea* (Zhang Licheng, Li Yanmei, Yuan Yashu, et al, Research On the Screening and characteristics of Nitrosation Denitrifying Dephosphorization of Five Strains of Phosphate Accumulating Organisms, Industrial Water Treatment, 2012, 32(4): 33-35), *Acinetobacter* (Acevedo B, Camiña C, Corona J E, et al., the Metabolic Versatility of PAOs As an Opportunity to Obtain a Highly P-enriched Stream for Further P-recovery, Chemical Engineering Journal, 2015, 270: 459-467), *Aeromonas, Pseudomonas, Streptococcus, Moraxella* and *Micrococcus* (We Ruping, Yancheng, Yang xinyan, et al, Research Progress on the Functional Microorganisms in Enhanced Biological Phosphorus Removal (EBPR) Systems, Biotechnology Bulletin, 2017, 33(10): 1-8). However, in addition to low tolerance to natural environment, difficulty in breeding and culturing, easily declined activity and low viable count in actual use, the majority of these strains show low phosphorus removal efficiency in the actual process, therefore, the phosphorus removal efficiency is expected to be improved.

SUMMARY

To resolve the abovementioned technical problem, the invention provides an efficient phosphorus accumulating *Novosphingobium* sp. The strain of the *Novosphingobium* sp is separated from activated sludge from domestic wastewater in the campus of the Wenzhou University in Wenzhou City, Zhejiang Province through a conventional separation process. Upon 16SrDNA sequence determination and comparative analysis on the sequenced result through GenBank Blast, it is found that, the strain has the homology as high as 99% with *Novosphingobium* sp. BH-4 (MG855668.1), and is thus identified as *Novosphingobium* sp., and numbered as *Novosphingobium* sp. SJB007.

The invention provides an efficient phosphorus accumulating *Novosphingobium* sp, and its strain is the *Novosphingobium* sp. SJB007 preserved in the China General Microbiological Culture Collection Center (CGMCC) with an access number of CGMCC No. 21177.

The invention also provides an application of the above *Novosphingobium* sp. SJB007 in removal of phosphorus from wastewater.

The invention also provides a method of removing phosphorus from wastewater by using the above *Novosphingobium* sp. SJB007, including the following steps:

(1) strain culture: inoculating the *Novosphingobium* sp. SJB007 into a seed culture medium, culturing for 24 h at a temperature of 15-35° C. and at a revolution speed of 150-180 rpm, centrifuging to obtain thallus, and washing the thallus with sterile water to prepare into a bacterial suspension with OD600 of 0.50-0.60;

(2) fermenting to remove phosphorus: inoculating the bacterial suspension prepared in the step (1) into phosphorus-containing wastewater, and fermenting at a pH of 4-8 and at a temperature of 15-35° C. to remove phosphorus, wherein a volume ratio of the bacterial suspension to the pig farm wastewater is 1:50.

Further, the seed culture medium in the step (1) includes the following components: 1.0 g of yeast powder, 1.0 g of NaCl, 0.3 g of $KH_2PO_4$, 0.25 g of $K_2HPO_4$, 0.2 g of $MgSO_4 \cdot 7H_2O$ and 1.0 g of glucose, the final volume is adjusted to 1000 mL with distilled water, and the pH is adjusted to 7.0 with a 1 mol/L NaOH aqueous solution or 1 mol/L HCL.

Further, in the step (1), culture is carried out at a temperature of 30° C. and at a revolution speed of 160 rpm.

Further, in the step (2), fermenting is carried out at a pH of 5-8 and at a temperature of 25-30° C.

Further, in the step (2), fermenting is carried out at a revolution speed of a shaker being 80-200 r/min.

The invention has the following technical effects:

1. The efficient phosphorus accumulating strain *Novosphingobium* sp. SJB007 provided by the invention is firstly reported in China.

2. According to the efficient phosphorus accumulating strain *Novosphingobium* sp. SJB007 provided by the invention, the appropriate temperature under which phosphorus is removed from phosphorus-containing wastewater is 15-35° C., and the temperature application scope is wide.

3. The efficient phosphorus accumulating strain *Novosphingobium* sp. SJB007 provided by the invention has a high removal rate of more than 97% when the concentration of phosphorus in the wastewater is 10-30 mg/L under an appropriate condition.

4. The efficient phosphorus accumulating strain *Novosphingobium* sp. SJB007 provided by the invention is wide in adaptation range, good in phosphorus removal efficiency under an aerobic condition, and great in application potential in actual phosphorus removal from wastewater.

DESCRIPTION OF THE EMBODIMENTS

Figure 1:
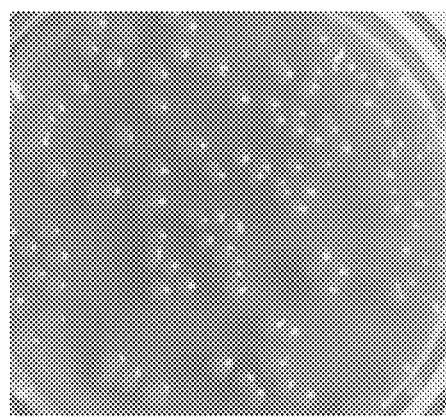
FIG. 1 shows a colony of the *Novosphingobium* sp. SJB007.

To make the objects, technical solutions and advantages of the present invention more clear, the invention will be further described in detail in the following embodiments in conjunction with the appended drawings.

The invention provides an efficient phosphorus accumulating *Novosphingobium* sp. The strain of the *Novosphingobium* sp is separated from activated sludge of domestic wastewater in the campus of the Wenzhou University in Wenzhou City, Zhejiang Province through a conventional separation process. Upon 16SrDNA sequence determination and comparative analysis on the sequenced result through GenBank Blast, it is found that, the strain has the homology as high as 99% with the *Novosphingobium* sp. BH-4 (MG855668.1), and is thus identified as *Novosphingobium* sp., and numbered as *Novosphingobium* sp. SJB007.

For experimental methods without any indicated specific conditions, conventional methods and conditions may be preferred. Otherwise, a descriptive literature shall be used for reference upon selection.

The seed culture medium used in Examples includes the following:

An enrichment medium and a seed medium: 1.0 g of yeast powder, 1.0 g of NaCl, 0.3 g of $KH_2PO_4$, 0.25 g of $K_2HPO_4$, 0.2 g of $MgSO_4 \cdot 7H_2O$ and 1.0 g of glucose, the final volume is adjusted to 1000 mL with distilled water, and pH is 7.0.

An isolation medium: 1.0 g of yeast powder, 1.0 g of NaCl, 0.3 g of $KH_2PO_4$, 0.25 g of $K_2HPO_4$, 0.2 g of $MgSO_4 \cdot 7H_2O$, 1.0 g of glucose and 20.0 g of agar, the final volume is adjusted to 1000 mL with distilled water, and pH is 7.0.

A polyphosphate granular dyeing medium: 4.0 g of $Na_3C_6H_5O_7 \cdot 2H_2O$, 0.5 g of NaCl, 2.5 g of $(NH_4)_2SO_4$, 0.25 g of $CaCl_2$, 0.25 g of $MgSO_4 \cdot 7H_2O$, 12.8 g of $Na_2HPO_4$, 3 g of $KH_2PO_4$, 0.01 g of maltose and 0.025 g of toluidine blue O, the final volume is adjusted to 1000 mL with distilled water, and pH is 7.0.

A polyphosphate medium: 10 g of glucose, 0.5 g of $(NH_4)_2SO_4$, 0.3 g of KCl, 0.3 g of NaCl, 0.03 g of $FeSO_4 \cdot 7H_2O$, 0.03 g of $MnSO_4 \cdot H_2O$, 5 g of $CaCO_3$ and 0.0439 g of $KH_2PO_4$, the final volume is adjusted to 1000 mL with distilled water, and pH is 7.0.

Example 1 Separation and Identification of the *Novosphingobium* sp. SJB007

I. Separation and Screening of Strains

A sample is activated sludge of domestic wastewater from the campus of the Wenzhou University in Wenzhou City, Zhejiang Province. By use of a conventional separation process, a certain amount of activated sludge was added into a 250 mL conical flask containing 100 mL of an enrichment medium at a ratio of 10%, and then subjected to shaking culture for a week at a temperature of 30° C. and a revolution speed of 160 rpm. A properly diluted bacterial solution was coated on an isolation medium, culturing was carried out for 48 h at a temperature of 30° C., a single colony was transferred into a new isolation medium for streaking purification until a pure culture was obtained through microscopic examination. The pure culture was transferred and preserved at a temperature of 4° C.

The preserved strains were respectively inoculated to seed culture medium for culturing for 24 h (a 250 mL conical flask contains 100 ml of a medium) at a temperature of 30° C. and a revolution speed of 150 rpm.

180 μL of the polyphosphate granular dyeing medium and 20 μL of the bacterial solution were added on a 96-well plate, while same amount of sterile water was added to a control group. Culturing was carried out for 48 h at a temperature of 30° C. If polyphosphate granules were formed in test strains, toluidine blue entered thallus to react with and color the thallus, concentration of toluidine blue in wells decreased, and color became lighter. More clear discoloration represents higher phosphorus accumulating capability of strains. Based on color changes, the phosphorus accumulating strain which discolors the toluidine blue more clearly is named as SJB007, and then further purified, with its colony morphology shown in FIG. 1. It is seen from FIG. 1 that, the colony is circular, well-bordered, yellow and opaque; and its surface is smooth, wet and viscous, and its middle is bulged.

II. Molecular Identification of Strains

The target strains were cultured for 24 h on a slant medium, genome DNA was extracted, and 16S rDNA of the strains was amplified by the PCR technology. The used primers include a forward primer (5'-CAGAGTTT-GATCCTGGCT-3') and a reverse primer (5'-AGGAGGT-GATCCAGCCGCA-3').

The composition of a PCR reaction system is shown in the table below:

| Reagent | Volume (μl) |
| --- | --- |
| Template (genome DNA 20-50 ng/μl) | 0.5 |
| 100 * Buffer (including $Mg^{2+}$) | 2.5 |
| dNTP(2.5 mM) | 1.0 |
| Forward primer (10 μM) | 0.5 |
| Reverse primer (10 μM) | 0.5 |
| Taq enzyme | 0.2 |
| Double distilled water | 19.8 |

PCR conditions are shown in the table below:

| Temperature | Time | Program |
| --- | --- | --- |
| 94° C. | 4 min | Predegeneration |
| 94° C. | 45 sec | 30 cycles |
| 55° C. | 45 sec | |
| 72° C. | 1 min | |
| 72° C. | 10 min | Repair extension |
| 4° C. | ∞ | Termination reaction |

Figure 2:
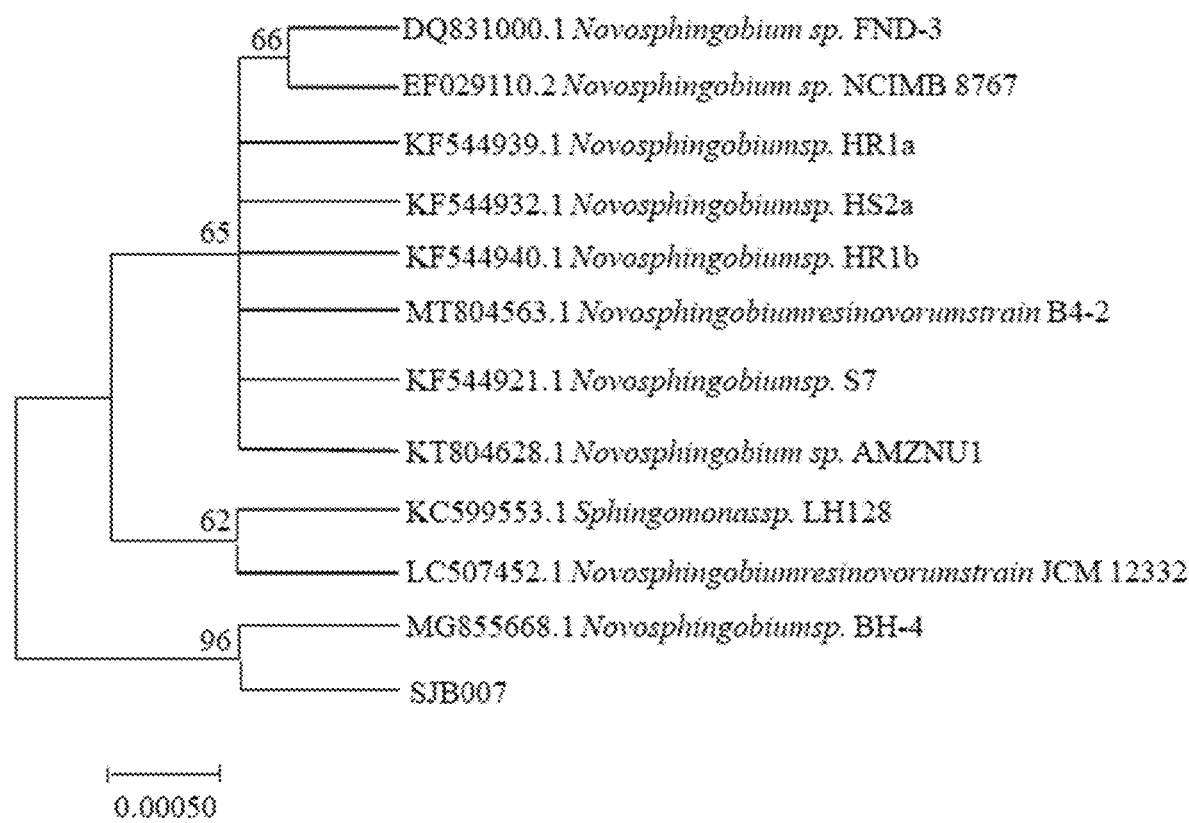
FIG. 2 shows a phylogenetic tree of a strain SJB007 and 16SrDNA of relevant species by proximity ligation assay through MEGA 4.1 software.

5 μL of a PCR product was taken for 1% agarose electrophoresis (150 V, 100 mA, 20 min), and it was qualified when amplified segments were about 1.5 kb long through electrophoresis detection. The qualified PCR product was purified by a SanPrep column PCR product purification kit, and sequenced by the Sangon Biotech (shanghai) Co., Ltd. The sequenced 16S rDNA sequence and that in the GenBank database were subjected to homology comparison, with the result shown in FIG. 2. It is clearly seen from FIG. 2 that, the strain has the highest homology up to 99% with the *Novosphingobium* sp. BH-4 (GenBank accession No. MG855668.1), and thus identified as *Novosphingobium* sp., and numbered as *Novosphingobium* sp. SJB007.

The *Novosphingobium* sp. SJB007 was preserved in the China General Microbiological Culture Collection Center (CGMCC) on 13 Nov. 2020 with an access number of CGMCC No 0.21177, and the preservation address is No. 3, Yard 1, Beichen West Road, Chaoyang District, Beijing.

Example 2 Phosphorus Removal Characteristics of the *Novosphingobium* sp. SJB007

The preserved strain was inoculated into a 250 ml conical flask containing a 100 ml of a seed culture medium, cultured for 24 h at a temperature of 30° C. and at a revolution speed of 150 r/min, centrifuged for 10 min at a revolution speed of 5000 r/min, washed twice with sterile water, and prepared into a bacterial suspension with sterile water (OD600=0.5-0.6); the bacterial suspension was transferred into a 250 mL conical flask containing a 100 mL of a polyphosphate medium at a volume ratio of the bacterial suspension to the polyphosphate medium of 1:50, cultured for 24 h at a certain temperature and revolution speed and centrifuged for 10 min at a revolution speed of 14000 r/min; a supernate was collected; and phosphorus concentration was determined by a Mo—Sb anti-spectrophotometric method as stipulated by GB 11893-1989. Phosphorus removal rate is calculated with the following formula: Phosphorus removal rate (%)=(initial concentration of phosphorus in wastewater−concentration of phosphorus in wastewater after strain culture)/initial concentration of phosphorus in wastewater×100

According to the above method, influences on phosphorus removal of the *Novosphingobium* sp. SJB007 from pH, temperature, revolution speed of a shaker and phosphorus concentration are mainly researched.

1. Selection of pH

A polyphosphate medium with a phosphorus concentration of 10 mg/L was prepared, pH was adjusted to 4, 5, 6, 7, 8, 9 or 10 respectively, a seed solution at a volume ratio of the seed solution to the polyphosphate medium of 1:50 was inoculated, culturing was carried out for 24 h at a temperature of 30° C. and a revolution speed of 160 rpm, centrifugation was carried out for 10 min at a revolution speed of 14000 r/min, a supernate was collected, and phosphorus concentration was determined with the result shown in the table below. It is seen from the table that, the strain SJB007 has a good phosphorus removal rate of over 97% for wastewater at a pH range of 4-8.

| pH | 4 | 5 | 6 | 7 | 8 | 9 | 10 |
|---|---|---|---|---|---|---|---|
| Phosphorus removal rate (%) | 97.713 | 98.140 | 98.980 | 99.827 | 98.140 | 62.117 | 3.636 |

2. Selection of Culture Temperature

A polyphosphate medium with a phosphorus concentration of 10 mg/L was prepared, pH was adjusted to 7, a seed solution at a volume ratio of the seed solution to the polyphosphate medium of 1:50 was inoculated, culturing was carried out for 24 h respectively at the temperature of 15° C., 20° C., 25° C., 30° C. or 35° C. and at a revolution speed of 160 rpm, centrifugation was carried out for 10 min at a revolution speed of 14000 r/min, a supernate was collected, and a phosphorus concentration was determined with the result shown in the table below. It is seen from the table that, the strain SJB007 has a good phosphorus removal rate of over 97% for wastewater at a temperature range of 15-35° C.

| Temperature (° C.) | 15 | 20 | 25 | 30 | 35 |
|---|---|---|---|---|---|
| Phosphorus removal rate (%) | 98.983 | 97.713 | 99.407 | 98.983 | 98.133 |

3. Selection of Revolution Speed of a Shaker

A polyphosphate medium with a phosphorus concentration of 10 mg/L was prepared, pH was adjusted to 7, a seed solution at a volume ratio of the seed solution to the polyphosphate medium of 1:50 of 2% was inoculated, culturing was carried out for 24 h at a temperature of 30° C. and respectively at a revolution speed of 80, 120, 160 or 200 rpm, centrifugation was carried out for 10 min at a revolution speed of 14000 r/min, a supernate was collected, and a phosphorus concentration was determined with the result shown in the table below. It is seen from the table that, the strain SJB007 has a good phosphorus removal rate of over 97% for wastewater at a revolution speed range of 80-200 r/min.

| | Revolution speed (r/min) of the shaker | | | |
|---|---|---|---|---|
| | 80 | 120 | 160 | 200 |
| Phosphorus removal rate (%) | 97.713 | 97.713 | 98.983 | 98.133 |

Example 3 Effect of Removal of Phosphorus from Pig Farm Wastewater after Anaerobic Treatment by the *Novosphingobium* sp. SJB007

The bacterial suspension of the *Novosphingobium* sp. SJB007 prepared according to the method in Example 2 was respectively transferred into 200 mL of pig farm wastewater after anaerobic treatment and cultured at a temperature of 25° C. and a revolution speed of 160 r/min, wherein the original wastewater in which no bacterial suspension was inoculated was used as a control group to be cultured under same conditions, and a volume ratio of the bacterial suspension to the pig farm wastewater is 1:50. Culturing was carried out for 24 h, centrifugation was carried out for 10 min at a revolution speed of 14000 r/min, a supernate was collected, and a phosphorus concentration was determined. The concentration of phosphorus in pig farm wastewater after anaerobic treatment is 3.12 mg/L, but it declines to 1.57 after cultured by the *Novosphingobium* sp. SJB007, and the removal rate is 49.68%; the concentration of phosphorus in the control group is 2.91 mg/L, lowered by 6.73%. Therefore, the strain *Novosphingobium* sp. SJB007 has a great application potential in removal of phosphorus from phosphorus-containing wastewater in actual use.

What is claimed is:

1. A method of removing phosphorus from wastewater by using *Novosphingobium* sp. SJB007 with an access number of CGMCC NO. 21177, comprising the following steps:

(1) strain culture: inoculating the *Novosphingobium* sp. SJB007 into a seed culture medium, culturing for 24 h at a temperature of 15-35° C. and at a revolution speed of 150-180 rpm, centrifuging to obtain thallus, and washing the thallus with sterile water to prepare into a bacterial suspension with OD600 of 0.50-0.60; and (2) fermenting to remove phosphorus: inoculating the bacterial suspension prepared in the step (1) into phosphorus-containing pig farm wastewater, and fermenting at a pH of 4-8 and at a temperature of 15-35° C. to remove phosphorus, wherein a volume ratio of the bacterial suspension to the pig farm wastewater is 1:50.

2. The method according to claim 1, wherein the seed culture medium in the step (1) comprises the following components: 1.0 g of yeast powder, 1.0 g of NaCl, 0.3 g of $KH_2PO_4$, 0.25 g of $K_2HPO_4$, 0.2 g of $MgSO_4·7H_2O$ and 1.0 g of glucose, a final volume is adjusted to 1000 mL with distilled water, and pH is adjusted to 7.0 with a 1 mol/L NaOH aqueous solution or 1 mol/L HCL.

3. The method according to claim 1, wherein in the step (1), culture is carried out at a temperature of 30° C. and at a revolution speed of 160 rpm.

4. The method according to claim 1, wherein in the step (2), fermenting is carried out at a pH of 5-8 and at a temperature of 25-30° C.

5. The method according to claim 1, wherein in the step (2), fermenting is carried out at a revolution speed of a shaker being 80-200 r/min.

* * * * *

SEQUENCE LISTING

<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: Synthesized forward primer for 16S rDNA
      amplification

<400> SEQUENCE: 1
cagagtttga tcctggct                                                    18

<210> SEQ ID NO 2
<211> LENGTH: 19
<212> TYPE: DNA
<213> ORGANISM: Artificial Sequence
<220> FEATURE:
<223> OTHER INFORMATION: Synthesized reverse primer for 16S rDNA
      amplification

<400> SEQUENCE: 2
aggaggtgat ccagccgca                                                   19